(12) United States Patent
Ugander et al.

(10) Patent No.: US 8,008,538 B2
(45) Date of Patent: Aug. 30, 2011

(54) MECHANICAL BARRIER IN WOUND HEALING

(75) Inventors: Martin Ugander, Malmö (SE); Malin Malmsjö, Lund (SE)

(73) Assignee: Forskarpatent I Syd AB, Lund (SE)

( * ) Notice: Subject to any disclaimer, the term of this patent is extended or adjusted under 35 U.S.C. 154(b) by 150 days.

(21) Appl. No.: 11/747,984

(22) Filed: May 14, 2007

(65) Prior Publication Data
US 2007/0260207 A1    Nov. 8, 2007

Related U.S. Application Data

(63) Continuation of application No. PCT/SE2007/000173, filed on Feb. 27, 2007.

(51) Int. Cl.
*A61F 13/00* (2006.01)
*A61F 5/44* (2006.01)

(52) U.S. Cl. ............ 602/47; 604/305; 604/337

(58) Field of Classification Search ........ 604/42, 604/43, 44, 45, 46, 47, 48, 50, 51, 52, 53, 604/289, 290, 355, 337; 128/897, 898; 602/42, 602/43, 44, 45, 46, 47, 48, 50, 51, 52, 53; 600/37

See application file for complete search history.

(56) References Cited

U.S. PATENT DOCUMENTS

| | | | |
|---|---|---|---|
| 5,636,643 A * | 6/1997 | Argenta et al. | 128/897 |
| 6,254,580 B1 * | 7/2001 | Svedman | 604/313 |
| 6,390,976 B1 * | 5/2002 | Spence et al. | 600/210 |
| 6,506,149 B2 * | 1/2003 | Peng et al. | 600/37 |
| 6,855,135 B2 * | 2/2005 | Lockwood et al. | 604/313 |
| 7,226,409 B2 * | 6/2007 | Peng et al. | 600/37 |
| 2003/0040687 A1 | 2/2003 | Boynton et al. | |
| 2003/0109855 A1 * | 6/2003 | Solem et al. | 604/540 |
| 2007/0203510 A1 * | 8/2007 | Bettuchi | 606/153 |

FOREIGN PATENT DOCUMENTS

| | | |
|---|---|---|
| EP | 1652549 | 5/2006 |
| WO | 03057071 | 7/2003 |

OTHER PUBLICATIONS

Banwell, "Topical negative pressure (TNP): the evolution of a novel wound therapy" Journal of Wound Care, vol. 12, No. 1, Jan. 2003, pp. 22-28.

Banwell et al., "Topical negative pressure (TNP): the evolution of novel wound therapy", Abstract, PubMed, J. Wound Care, 2003, 1 page.

Morykwas et al., "Vacuum-Assisted Closure: State of Basic Research and Physiologic Foundation", American Society of Plastic Surgeons, 2006, www.plasreconsurg.org, pp. 121S-126S.

(Continued)

*Primary Examiner* — Patricia M Bianco
*Assistant Examiner* — Ophelia Hawthorne
(74) *Attorney, Agent, or Firm* — Gesmer Updegrove LLP

(57) ABSTRACT

The present invention relates to an implantable, disposable barrier disc to be used in negative pressure treatment of wounds, in particular sternotomy wounds, wherein the barrier disc consists of a rigid material withstanding a negative pressure of at least −50 mmHg without causing deformation to the barrier disc, and that the barrier disc is perforated to allow drainage of wound fluid through said barrier disc.

14 Claims, 12 Drawing Sheets

OTHER PUBLICATIONS

Sartipy et al., "Cardiac Rupture During Vacuum-Assisted Closure Therapy", Case Report, the Society of Thoracic Surgeons, Elsevier Inc., 2006, pp. 1110-1111.

Bapat et al., "Experience with Vacuum-Assisted Closure of Sternal Wound Infection Following Cardiac Suregery and Evaluation of Chronic Complications Associated with its Use", J. Card Surg, 2008, 23, pp. 227-233.

Ennker et al., "The concept of negative pressure wound therapy (NPWT) after poststernotomy mediastinitis-a single center experience with 54 patients", J. Card. Surg., 2009, 4:5, pp. 1-8.

Malmsjo et al., "Preventing heart injury during negative pressure wound therapy in cardiac surgery: Assessment using real-time magnetic resonance imaging", The Journal of Thoracic and Cardiovascular Surgery, 2009, pp. 1-7.

FDA Preliminary Public Heath Notificiation: Serious Complications Associated with Negative Pressure Wound Therapy Systems, http://www.fed.gov/MedicalDevices/Safety/AlertsandNotices/PublicHealthNotifications/ucm190658.htm#table1, 2009, pp. 1-4.

\* cited by examiner

MECHANICAL BARRIER IN WOUND HEALING

PRIORITY INFORMATION

The present application is a continuation of PCT Application No. PCT/SE07/000173 filed on Feb. 27, 2007, that claims priority to Swedish Application No. SE 060097-0, filed on Apr. 26, 2006, both of which are incorporated herein by reference in their entireties.

DESCRIPTION

1. Technical Field

The present invention relates to a device to be used in topical negative pressure treatment of wounds in particular sternotomy wounds.

2. Background of the Invention

In cardiac surgery, e.g., by-pass operation of the heart, the sternum is cut lengthwise, and quite often the left pleura is opened as well. This generates a so called sternotomy wound. Following surgery, the sternotomy wound is closed with sternal wires and left to heal. In a number of patients, about 1 to 5% of those undergoing cardiac surgery including sternotomy, an infection called mediastinitis occurs. Such poststernotomy mediastinitis occurs in particular in a risk group of patients, such as those suffering from diabetes mellitus, low left ventricular ejection fraction, obesity, renal failure, and three-vessel disease.

Established treatment of poststernotomy mediastinitis includes debridement with frequent postoperative irrigation, change of wound dressings and direct secondary closure or secondary closure by use of vascularized muscle flaps. The reported early mortality using these established techniques in poststernotomy mediastinitis following coronary bypass surgery is between 8 and 25%. However, the introduction of a technique for using topical negative pressure (TNP) to treat poststernotomy mediastinitis has essentially reduced the mortality due to mediastinitis to 0% (Sjogren, J., et al. Ann Thorac Surg. 80: 1270, 2005).

The TNP technique entails applying negative pressure to a wound in a controlled manner. A wound dressing in the form of a sterile polyurethane foam is placed between the sternal edges but not below the level of the sternum, in order not to affect hemodynamic and respiratory function. A second layer of foam is often placed subcutaneously and secured with a running suture to the surrounding skin. This facilitates the application of the adhesive drape and reduces the risk of accidental movement of the device. Drainage tubes are inserted into the foam. The wound is then sealed with a transparent adhesive drape. The drainage tubes are connected to a purpose-built vacuum pump and a canister for collection of effluents. Initially, a low pressure (e.g. −50 mmHg) is applied to allow adjustment of the foam as the air is evacuated. If the wound geometry and foam contraction are considered satisfactory, a pressure of −125 mmHg is applied. Air leakage is known to dry out the wound and can be prevented by additional draping. Most of the patients can be extubated and mobilized immediately after TNP application. Revisions and dressing changes are performed regularity, e.g. three times a week, under aseptic conditions and general anesthesia. The sternal wound can be closed and rewired when the infection has resolved, typically after 1-3 weeks of TNP treatment. The method is simple and effective and is believed to combine the benefits of closed and open wound treatment to create an environment that promotes wound healing.

However, a very serious potential complication of TNP therapy of sternotomy wounds is the risk for serious damage to the heart and surrounding structures, in particular rupture of the right ventricle of the heart. Two cases of right ventricular rupture have been described in the literature (Abu-Omar, Y., et al. Ann Thorac Surg. 76: 974; author reply 974, 2003). A total of 36 cases of heart rupture have been reported as of February 2006 (unpublished data).

It is established that poststernotomy mediastinitis can be effectively treated using TNP, but it is a major concern that the method is not completely reliable and can cause heart rupture.

SUMMARY OF THE PRESENT INVENTION

The present invention discloses a device as well as a method for eliminating this problem, i.e., eliminating the risk for serious damage to underlying tissue, including heart rupture, at TNP treatment of different wounds, including sternotomy wounds.

DETAILED DESCRIPTION OF THE PRESENT INVENTION

The present invention in particular relates to a barrier disc to be placed underneath the opening of a wound, i.e. the underneath the sternum, preferably a rigid barrier disc, preferably a perforated barrier disc, preferably in an attached relationship to a, preferably foam, wound interface dressing.

By means of the present invention the underlying tissues, i.e. the heart and surrounding structures, are hindered from becoming sucked up in between the edges of the wound, i.e. the sternal edges, thereby preventing the underlying tissues from being damaged by the wound edges, i.e. right ventricular rupture from being wedged by the, many times, sharp edges of the sternum. In the case of a sternotomy wound, the heart, in particular the right ventricle, lung tissue and the by-pass grafts will be protected from the sternal edges. Furthermore, the barrier disc can protect the impairment of heart function via suction of the right ventricular free wall up into the gap between the sternal edges.

The present invention will now be described more in detail with reference to the following and the accompanying drawings showing preferred embodiments of the invention. In the drawing

The barrier disc as such may be flexible but so rigid that it does not become bent by a pressure amounting to −200 mmHg. I.e. the material shall be so rigid that the barrier disc cannot be sucked up in between the sternal edges, or become deformed in any other way.

The edges 2 of the barrier disc 1 are preferably of a less rigid structure. Thus these more flexible edges are allowed to adapt themselves to the inner side of the deep wound, i.e. the inner part of the sternum, and to provide a sealing of the barrier disc between the wound edges and the deeper structures inside the wound. The barrier disc 1 is perforated by means of a number of through going holes 3. These holes 3 have the function of allowing for passage of wound fluid being sucked from the interior of the wound to the drainage of the wound into drainage tubes. The drainage is made possible by the vacuum applied onto the top of the barrier disc by means of one or more suction tubes applied to a vacuum source, such as a vacuum pump.

Figure 1:
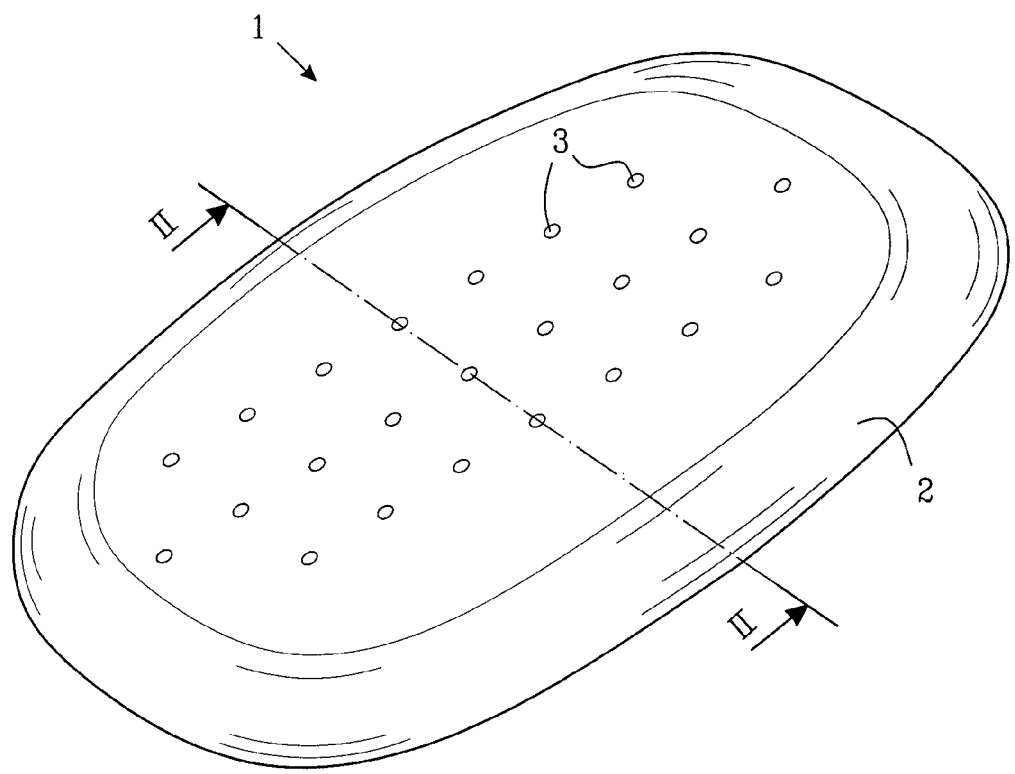
FIG. 1 shows a perspective view of a first embodiment of the invention.
Figure 2:
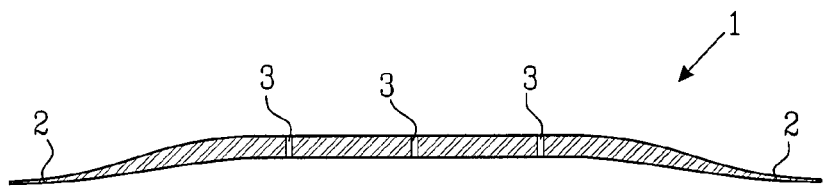
FIG. 2 shows a cross-section of the embodiment of FIG. 1 along line 11-11 therein.
Figure 3:
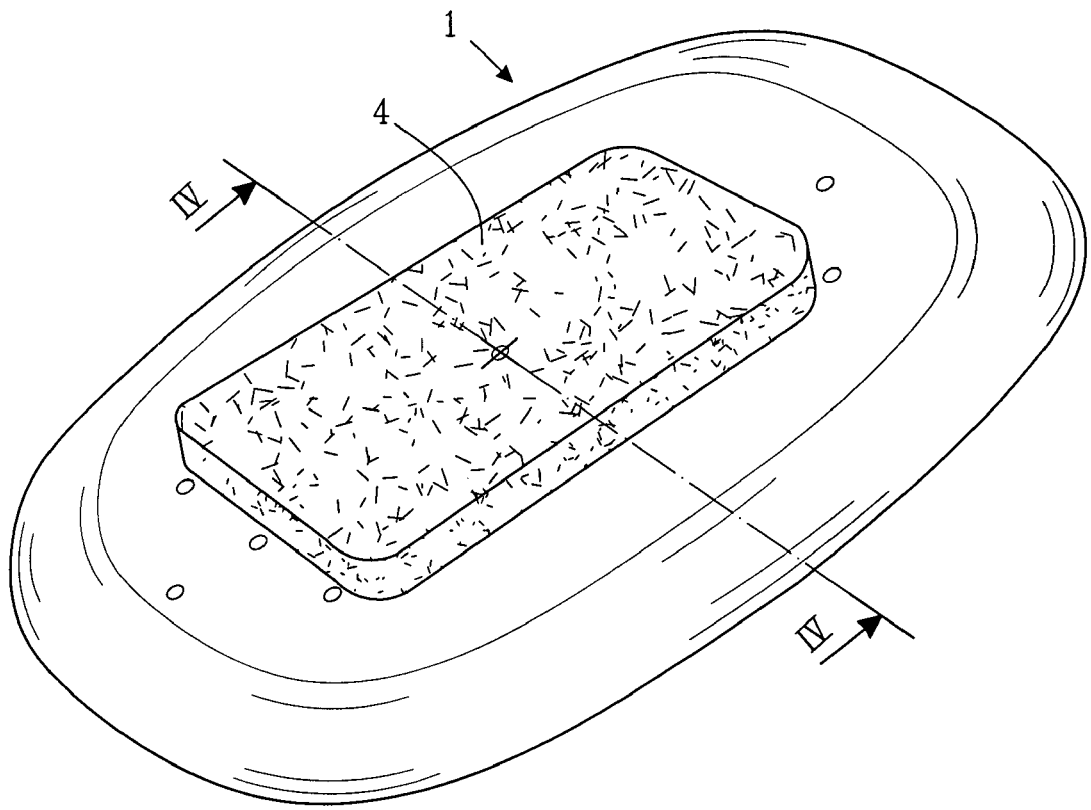
FIG. 3 shows a perspective view of a second embodiment of the invention.

FIG. 3 shows a second embodiment of the invention where a wound interface dressing material 4, such as a spongy foam polymer material has been attached to the top surface of the barrier disc 1. The barrier disc is attached to the wound dressing in order to insure that the barrier disc remains fixed in relation to the wound geometry. Hereby the wound dressing 4 has been attached via a thread 5 having a length of about the thickness of the sternum. The foam material has an open pore structure of 400 to 600 μm.

Figure 4:
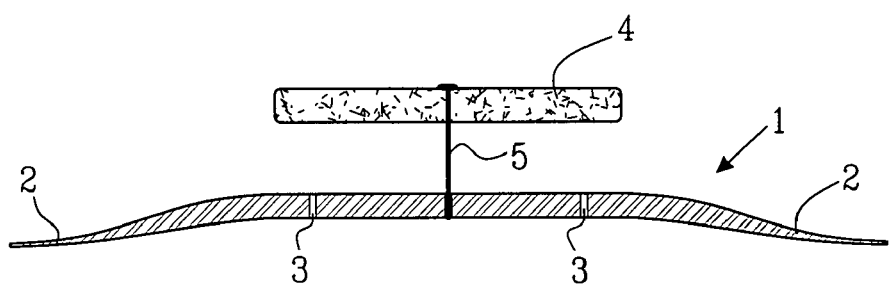
FIG. 4 shows a photograph of a sternum to which a spongy material is applied.
Figure 5:
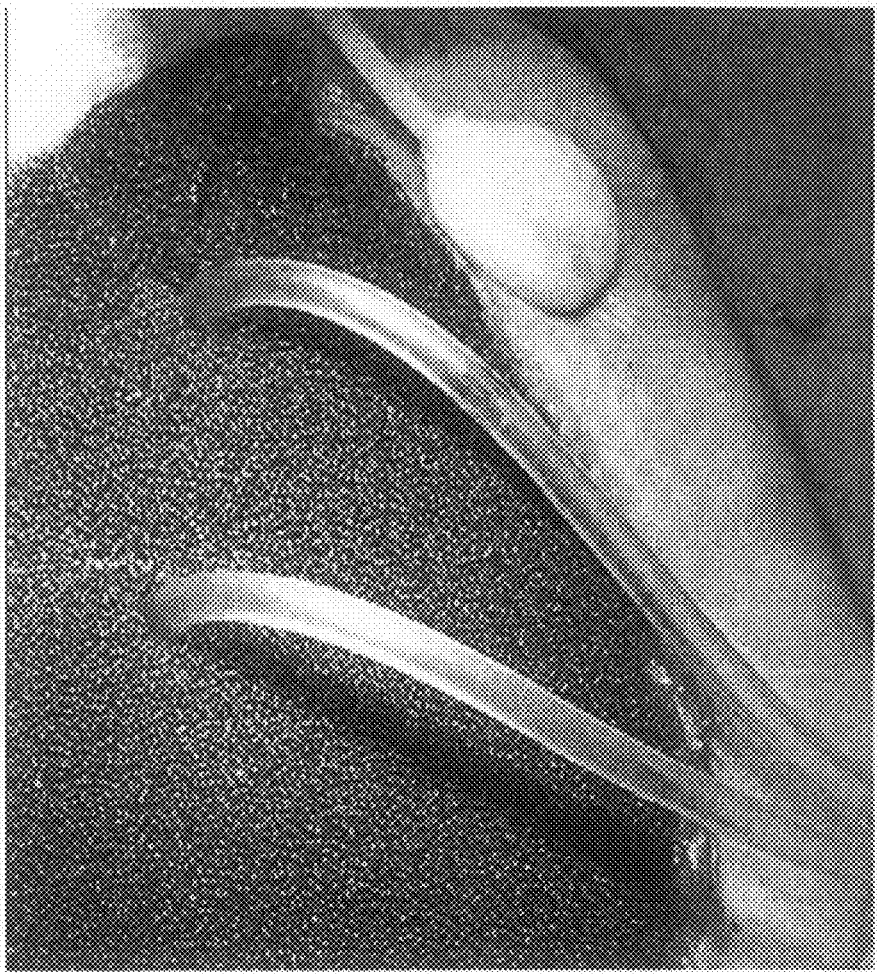
FIG. 5 shows the spongy material of FIG. 4 provided with suction tubes.

After surgery, the barrier disc 1 is applied underneath the sternum to cover the sternal edges and anterior of the barrier disc is a wound interface dressing that distributes the negative pressure to the wound surface, or as being a part of the barrier disc assembly on top of and over the sternal wound. Non-collapsible evacuation tubes are connected to the wound and the wound is sealed with adhesive drape is inserted into the center of the sternal foam layer (FIG. 4) and sutured in place. The superficial foam layer is sutured to the surrounding subcutaneous tissue (FIG. 5) and a skin protector (FIG. 6) is applied. The tubes are positioned 5 cm apart to facilitate application of adhesive draping around the tubes.

Figure 6:
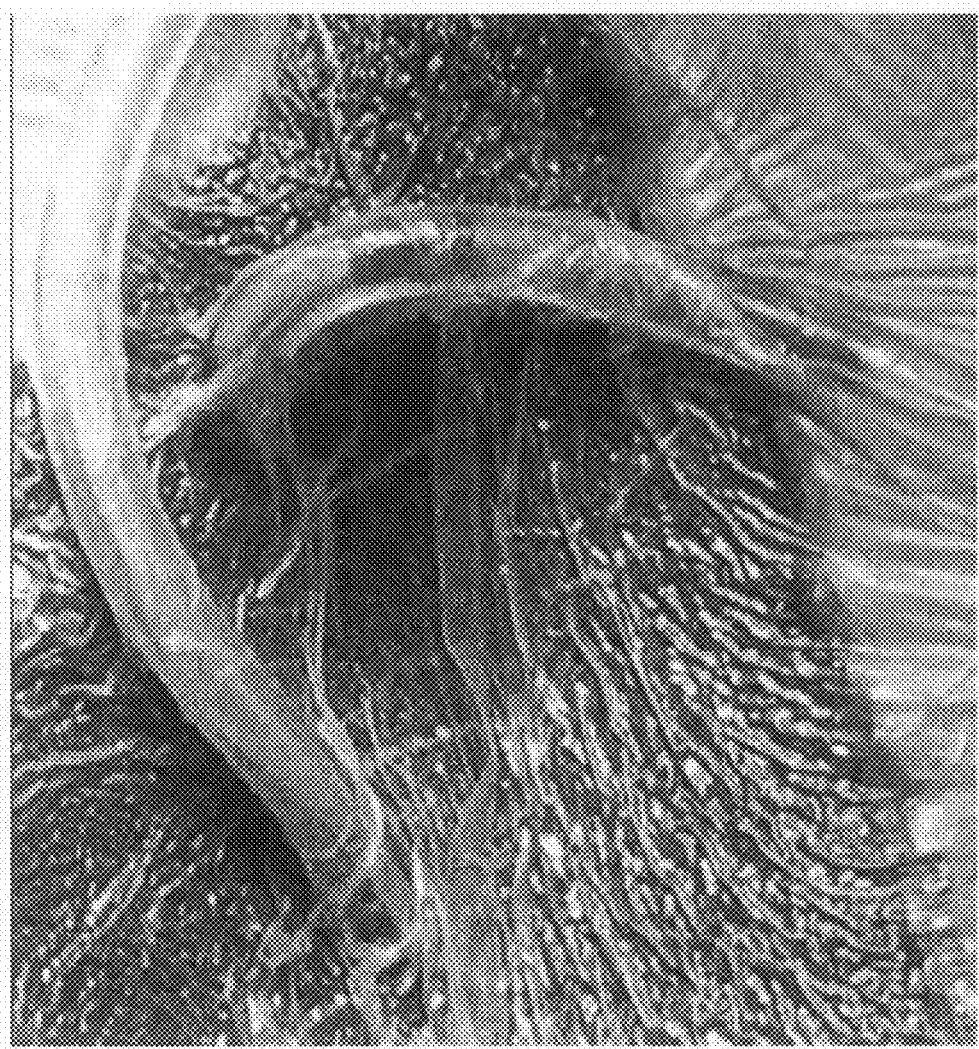
FIG. 6 shows the spongy material and tubes of FIG. 5 covered with a non-air permeable adhesive drape.

In a relaxed state the foam should protrude 1 to 2 cm over the edge of skin to allow volume reduction during vacuum therapy. The foam layer is then secured subcutaneously with a running suture to the surrounding skin edge. A second tube is normally inserted into the middle of this foam layer and sutured. A skin barrier disc protector (such as Cavilon; 3M HealthCare, St. Paul, Minn.) is applied (FIG. 5) and the open wound is sealed with a transparent adhesive drape (KCI, Copenhagen, Denmark). The drape overlaps the wound margins by 5 cm. The two drainage tubes are positioned 5 cm apart to facilitate application of the draping (FIG. 6). The two drainage tubes from the closed wound are connected to a vacuum source (VAC pump unit; KCI, Copenhagen, Denmark). This vacuum source set to deliver a continuous or intermittent negative pressure of −25 to −250 mmHg. Initially −50 mmHg is applied as it allows adjustment of the foam as the air is evacuated. If the wound geometry and foam contraction are considered to be satisfactory the pump unit is programmed to deliver −125 mmHg continuous negative pressure. At this pressure no further adjustment can be carried out since the compressed foam will be firm. A canister in the pump unit collects exudate from the wound. The wound dressings are changed regularly, e.g. every $3^{rd}$ day, under aseptic conditions and under general anesthesia. Bone and soft tissue necrosis is demarked by lack of granulation tissue on the sternal edges and complementary revisions are made during dressing change surgery.

Figure 7:
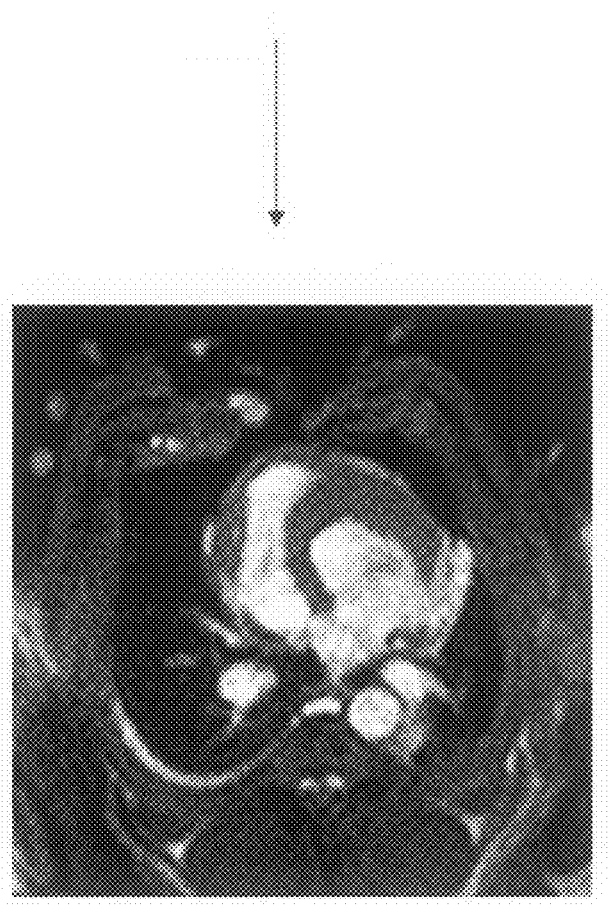
FIG. 7 shows a magnetic resonance (MR) image of a clinical test on pig before application of negative pressure.
Figure 8:
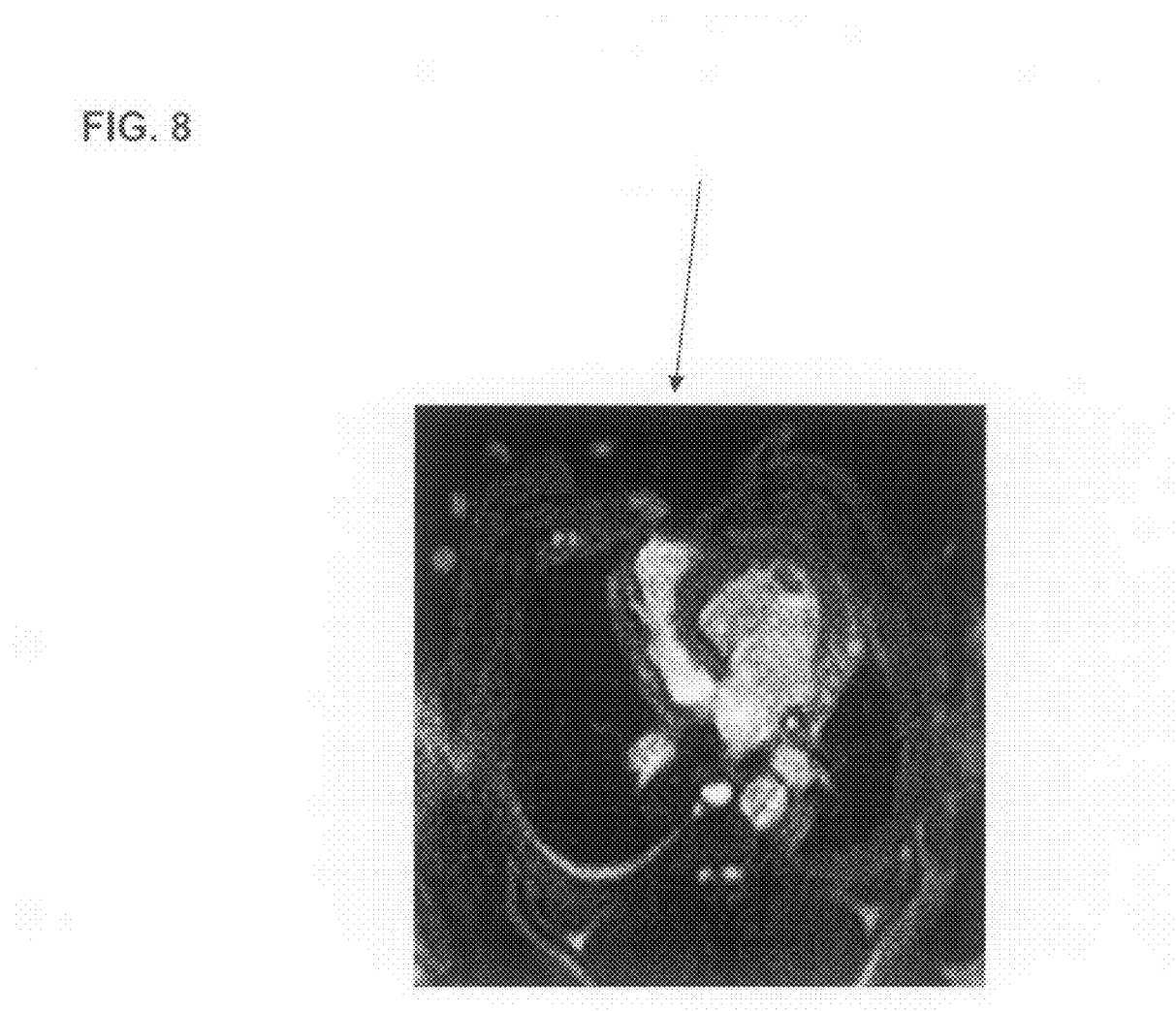
FIG. 8 shows a MR image of a clinical test of FIG. 7 at application of negative pressure.

FIG. 7 shows an image generated using Magnetic Resonance Imaging (MRI) in a clinical test on pig before application of negative pressure. The arrow in the figures points at the opening in the sternum. After having applied the negative pressure, FIG. 8, the sternum starts to close. The FIG. 8 also shows that the heart starts to turn sidewise.

Figure 9:
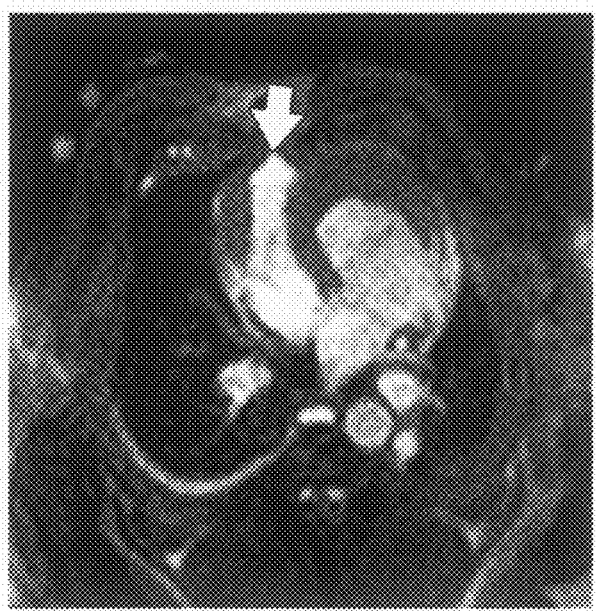
FIG. 9 shows a MR image of a clinical test of FIG. 7 at application of pressure amounting to −75 mmHg, whereby the heart is sucked up into the space between the sternal edges.

FIG. 9 shows the clinical test of FIG. 7 at application of pressure amounting to −75 mmHg, As shown at the point of the white arrow, the heart is sucked up into the space between the sternum edges and which might lead to impaired heart function.

Figure 10:
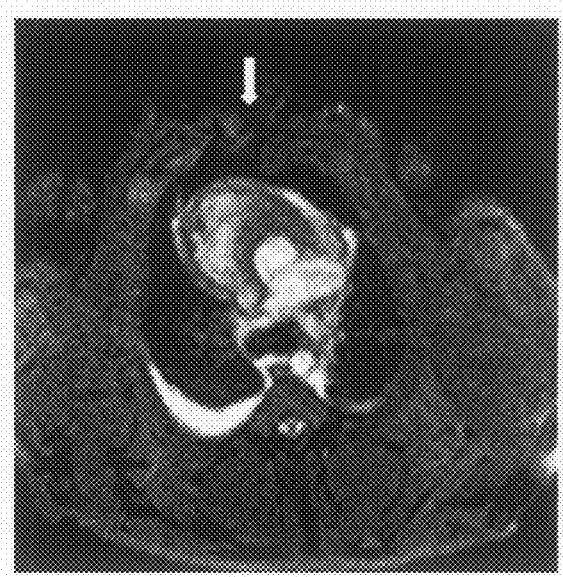
FIG. 10 shows a MR image of clinical test using a device of the present invention before application of negative pressure.
Figure 11:
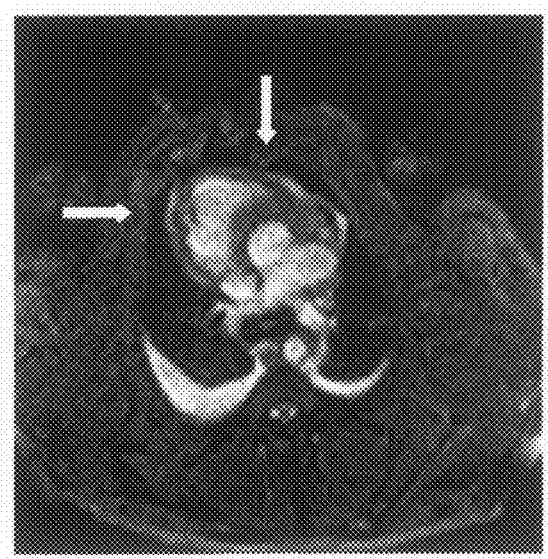
FIG. 11 shows a MR image of a clinical test using a device of the present invention of FIG. 10 at application of negative pressure.
Figure 12:
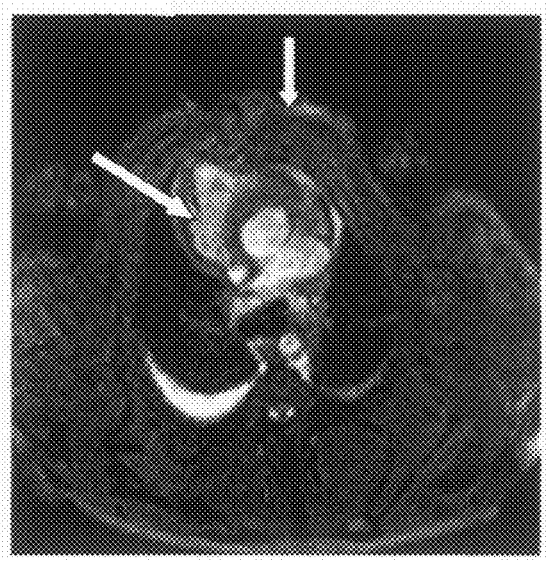
FIG. 12 shows a MR image of a clinical test using a device of the present invention of FIG. 10 at application of pressure amounting to −175 mmHg, whereby the device prevents the heart from being sucked up between the sternal edges.

FIG. 10 shows a clinical test, on a pig, using a device, the present invention before application of negative pressure. The device is present but not directly visible in the image because MRI only depicts structures containing water. In FIG. 11 the device of the present invention of FIG. 10 is shown at application of negative pressure, whereby it should be noted that the heart now starts to turn round, left arrow. FIG. 12 shows the clinical test using a device of the present invention of FIG. 10 at application of pressure amounting to −175 mmHg, whereby it is evident, vertical arrow, that the barrier disc prevents the heart from being sucked up between the sternum parts, left inclined arrow.

Figure 13:
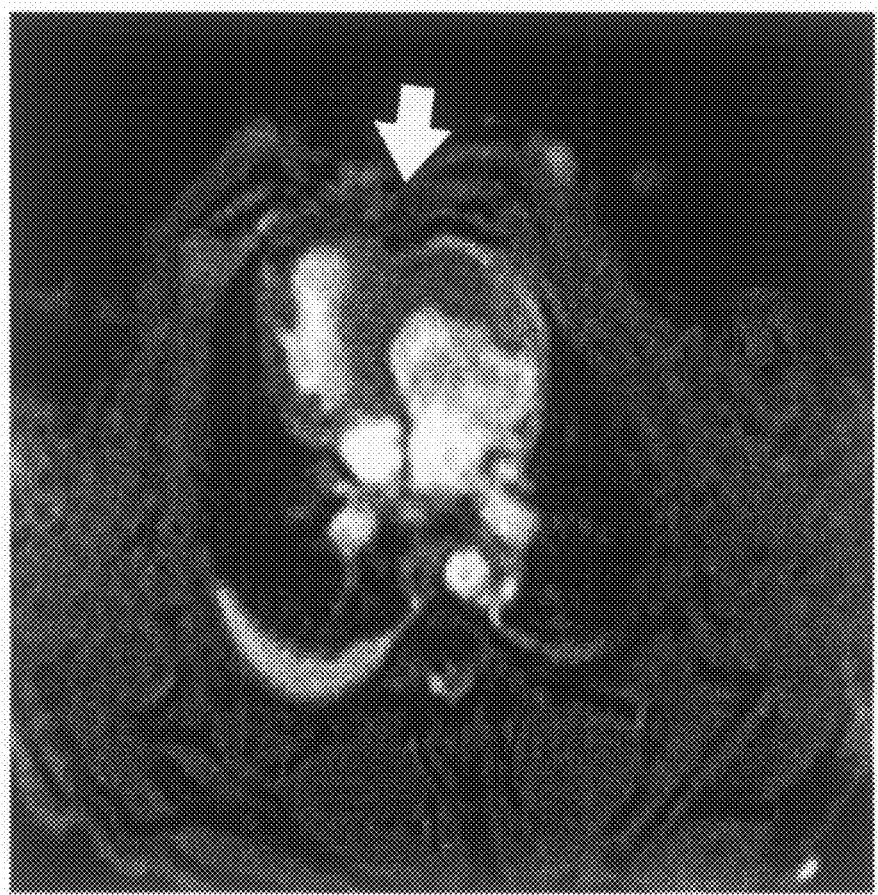
FIG. 13 shows a MR image of a clinical test in the absence of a device of the present invention and during the application of −125 mmHg pressure, whereby the sternal edge protrudes into the heart (white arrow)

FIG. 13 shows a clinical test, on a pig, in the absence of a device, the present invention, during the application of −125 mmHg pressure. One sternal edge protrudes markedly into the heart (white arrow).

Figure 14:
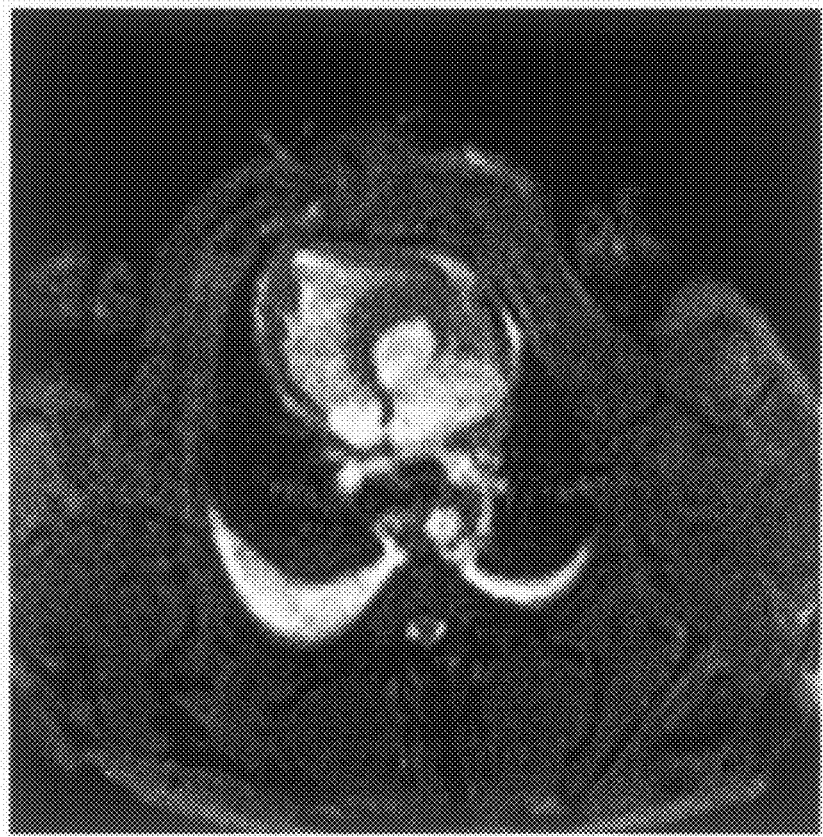
FIG. 14 shows a MR image of a clinical test with a device of the present invention of FIG. 13 during the application of −125 mmHg pressure, whereby the heart is protected from the sternal edges (white arrow), 1 denotes generally a substantially rectangular flat barrier disc made of a biocompatible material. The barrier disc is preferably made of a polymeric silicon material having a rigid structure. In order to fit the wound the barrier disc has a width of 10 to 15 cm and a length of 15 to 25 cm depending of the size of the patient. The barrier disc has preferably a thickness of 1 to 3 mm. Barrier discs for use with other wounds can be sized appropriately.

FIG. 14 shows a clinical test, on the same pig as in FIG. 13, using a device, the present invention, during the application of −125 mmHg pressure. The sternal edge no longer protrudes into the heart.

The invention claimed is:

1. An implantable, barrier disc for insertion over exposed organs or tissues during negative pressure treatment of wounds (NPWT), for preventing exposed organs or tissues from being exposed to harmful effects of the negative pressure, wherein the barrier disc is substantially flat, and comprises a rigid material withstanding a negative pressure of at least −50 mmHg, without causing deformation to the barrier disc, and that the barrier disc is perforated to allow drainage of fluid through said barrier disc, and has flexible edges that do not damage surrounding vital structures.

2. An implantable barrier disc according to claim 1, wherein the barrier disc is further attached to a wound interface dressing.

3. An implantable barrier disc according to claim 2, wherein the wound interface dressing is a spongy foam material consists of medical clinical foam material.

4. An implantable barrier disc according to claim 3, wherein the spongy foam material consists of polyurethane.

5. An implantable barrier disc according to claim 1, wherein the barrier disc is made of a biocompatible material.

6. An implantable barrier disc according to claim 5, wherein the biocompatible material is a clinical silicone material.

7. An implantable barrier disc according to claim 5, wherein the biocompatible material is a polylactic acid polymer or copolymer.

8. An implantable barrier disc according to claim 1, wherein the barrier disc withstands a negative pressure of at least −200 mmHg or greater negative pressure.

9. An implantable barrier disc according to claim 1, wherein the flexible edges are adapted to the surrounding inner wound contour at an application inside a wound.

10. An implantable barrier disc for placement over exposed organs and tissue during negative pressure treatment of wounds for preventing exposed organs or tissues from being exposed to harmful effects of the negative pressure, wherein the barrier disc comprises a rigid material withstanding a negative pressure of at least −50 mmHg without causing deformation to the barrier disc, and is perforated to allow drainage of fluid through said barrier disc and is flexible to not damage surrounding tissue structures.

11. An implantable barrier disc according to claim 10, wherein the barrier disc has flexible edges that do not damage surrounding vital structures.

12. An implantable barrier disc according to claim 11, wherein the flexible edges are adapted to the surrounding inner wound contour.

13. An implantable barrier disc according to claim 10, wherein the barrier disc withstands a negative pressure of at least −200 mmHg or greater negative pressure.

14. A method for protecting organs or tissue during negative pressure wound therapy comprising:
   providing an implantable, substantially flat, rigid and perforated barrier disc; and
   inserting an implantable, substantially flat, rigid and perforated barrier disc over the exposed organ for preventing the exposed organ or tissue from being exposed to harmful effects of the negative pressure, the said disc withstanding a negative pressure of at least −50 mmHg without causing deformation to the said disc and having flexible edges for not damaging surrounding tissues.

* * * * *